(12) United States Patent
Seo et al.

(10) Patent No.: US 10,481,188 B2
(45) Date of Patent: Nov. 19, 2019

(54) SYSTEM AND METHOD FOR NON-CONTACT MEASUREMENT OF OPTOELECTRONIC PROPERTIES OF THIN FILM

(71) Applicant: KOREA INSTITUTE OF SCIENCE AND TECHNOLOGY, Seoul (KR)

(72) Inventors: Minah Seo, Seoul (KR); Sanghun Lee, Seoul (KR); Chulki Kim, Seoul (KR); Q-Han Park, Seoul (KR); Jongho Choe, Seoul (KR); Jinsoo Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 94 days.

(21) Appl. No.: 15/874,415

(22) Filed: Jan. 18, 2018

(65) Prior Publication Data

US 2019/0086458 A1    Mar. 21, 2019

(30) Foreign Application Priority Data

Sep. 15, 2017    (KR) .......................... 10-2017-0118866

(51) Int. Cl.
    *G01R 27/00*    (2006.01)
    *G01R 27/26*    (2006.01)
    *G01N 21/3563*    (2014.01)

(52) U.S. Cl.
    CPC ..... *G01R 27/2682* (2013.01); *G01N 21/3563* (2013.01)

(58) Field of Classification Search
    CPC ........... G01N 21/3563; G01N 21/3581; G01N 21/8422
    USPC .......................................................... 324/629
    See application file for complete search history.

(56) References Cited

U.S. PATENT DOCUMENTS

2001/0029436 A1* 10/2001 Fukasawa .......... G01N 21/3581
                                              702/117
2006/0217830 A1*  9/2006 Saki ........................ C23C 16/52
                                              700/121

FOREIGN PATENT DOCUMENTS

| JP | 2002-098634 A | 4/2002 |
| JP | 2012-185116 A | 9/2012 |
| KR | 10-1334439 B1 | 11/2013 |
| KR | 10-1723449 B1 | 4/2017 |

OTHER PUBLICATIONS

Korean Office Action dated Mar. 14, 2018.

* cited by examiner

*Primary Examiner* — Melissa J Koval
*Assistant Examiner* — Courtney G McDonnough
(74) *Attorney, Agent, or Firm* — Rabin & Berdo, P.C.

(57) ABSTRACT

Disclosed herein is a system for non-contact measurement of an optoelectronic property. The system includes a sensing element configured to amplify an electromagnetic wave having a specific frequency, a thin film disposed on the sensing element such that an optoelectronic property of the thin film is measured, and an optoelectronic property measuring server configured to extract a physical property of the thin film based on the optoelectronic property of the thin film obtained when the electromagnetic wave amplified by the sensing element passes through the thin film.

15 Claims, 13 Drawing Sheets

SYSTEM AND METHOD FOR NON-CONTACT MEASUREMENT OF OPTOELECTRONIC PROPERTIES OF THIN FILM

CROSS-REFERENCE TO RELATED APPLICATION

This application claims priority to and the benefit of Korean Patent Application No. 2017-0118866, filed on Sep. 15, 2017, the disclosure of which is incorporated herein by reference in its entirety.

BACKGROUND

1. Field of the Invention

The present disclosure relates to a technique for measuring optoelectronic properties of a thin film, and more particularly, to a system and method for non-contact measurement of optoelectronic properties of a thin film, in which a doping level of a two-dimensional material is measured by an electromagnetic wave in a non-contact manner.

2. Discussion of Related Art

New two-dimensional materials exhibiting properties that are electrically and optically different from those of existing materials have attracted attention in the fields of semiconductor engineering and material engineering, and may be variously utilized in the field of semiconductors, electronics, batteries, or the like. That is, a two-dimensional material composed of a single atom layer is present in the form of a thin film of a few nanometers or less, and exhibits properties different from those of a typical bulk-type material, so the two-dimensional material has been newly spotlighted in the fields of semiconductor engineering and material engineering. However, it is difficult to measure physical properties of such type of materials due to restrictions caused by an extremely thin thickness and a shape of the materials. That is, since the two-dimensional material has a thin thickness similar to a single atom layer, properties of the two-dimensional material are remarkably changed due to external influences, so that an error may occur during electrical measurement due to contact of an electrode or a substrate with the two-dimensional material.

To solve such a problem, there has been proposed an optical reflection and transmission measurement scheme, which is a non-contact method. However, since an interaction length between a material and light is as short as a thickness of the material, it is difficult to observe signal modulation having a higher level in consideration of a signal-to-noise ratio of a measuring device, so attention has to be paid to an error during measurement and analysis. Therefore, for various applications of the two-dimensional material, a technique capable of precisely extracting physical properties through a highly-sensitive non-contact optical measuring method that compensates for disadvantages of the related art is required.

SUMMARY OF THE INVENTION

The present disclosure is directed to a system and method for non-contact measurement of optoelectronic properties of a thin film, in which the optoelectronic properties of the thin film, which is a two-dimensional material, may be measured through an optoelectronic property measuring method using a sensing element, and physical properties are precisely extracted based on the optoelectronic properties.

The present disclosure is directed to a system and method for non-contact measurement of optoelectronic properties of a thin film, in which a sensing element including a patterned slot engraved in the film or a patterned structure embossed on the film is used to sensitively measure the optoelectronic properties of the thin film by utilizing a local amplification phenomenon of an electromagnetic wave occurring on a surface of the slot or the structure.

According to a first aspect of the present disclosure, there is provided a system for non-contact measurement of an optoelectronic property, the system including: a sensing element configured to amplify an electromagnetic wave having a specific frequency; a thin film disposed on the sensing element such that an optoelectronic property of the thin film is measured; and an optoelectronic property measuring server configured to extract a physical property of the thin film based on the optoelectronic property of the thin film obtained when the electromagnetic wave amplified by the sensing element passes through the thin film.

Preferably, the sensing element may include: a substrate; and a film disposed on the substrate, wherein the film may include a patterned rectangular slot enbraved in the film or a patterned rectangular structure embossed on the film to amplify the electromagnetic wave having the specific frequency.

Preferably, the slot or the structure may have a width, a thickness, and a length, which are adjusted according to a frequency of an electromagnetic wave used for extracting the optoelectronic property of the thin film.

Preferably, the optoelectronic property measuring server may measure a transmittance based on transmission and reflection signals obtained when the amplified electromagnetic wave is optically transmitted through the thin film or reflected from the thin film.

Preferably, the optoelectronic property measuring server may calculate a permittivity of the thin film based on the measured transmittance.

Preferably, the optoelectronic property measuring server may extract a Fermi level, a charge density, or a charge mobility, which corresponds to the physical property of the thin film, based on the permittivity.

Preferably, the optoelectronic property measuring server may determine a doping level and an ion implantation amount of the thin film based on the physical property of the thin film.

According to a second aspect of the present disclosure, there is provided a method for non-contact measurement of an optoelectronic property performed in a system for non-contact measurement of an optoelectronic property, the method including: (a) measuring an optoelectronic property of a thin film obtained when an electromagnetic wave amplified by a sensing element, which is configured to amplify an electromagnetic wave having a specific frequency, passes through the thin film disposed on the sensing element; and (b) extracting a physical property of the thin film based on the measured optoelectronic property.

Preferably, step (a) may include measuring a transmittance based on transmission and reflection signals obtained when the amplified electromagnetic wave is optically transmitted through the thin film or reflected from the thin film.

Preferably, step (b) may include calculating a permittivity of the thin film based on the measured transmittance.

Preferably, step (b) may include extracting a Fermi level, a charge density, or a charge mobility, which corresponds to the physical property of the thin film, based on the permittivity.

Preferably, step (b) may include determining a doping level and an ion implantation amount of the thin film based on the physical property of the thin film.

Preferably, the sensing element may include: a substrate; and a film disposed on the substrate, wherein the film may include a patterned rectangular slot engraved in the film or a patterned rectangular structure embossed on the film to amplify the electromagnetic wave having the specific frequency.

Preferably, the slot or the structure may have a width, a thickness, and a length, which are adjusted according to a frequency of an electromagnetic wave used for extracting the optoelectronic property of the thin film.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
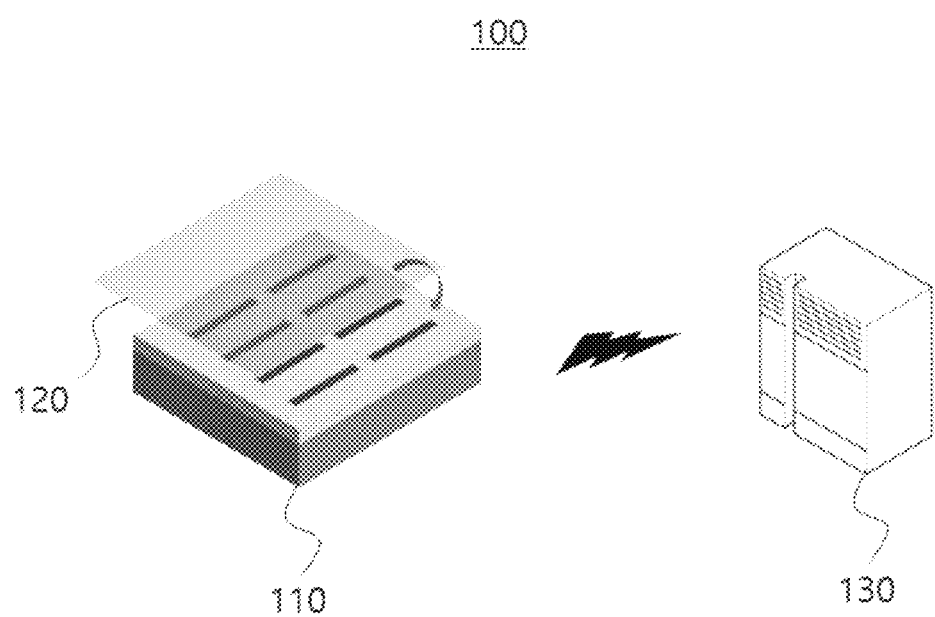
FIG. 1 is a configuration diagram of a system for non-contact measurement of optoelectronic properties of a thin film according to an exemplary embodiment of the present disclosure.

Hereinafter, advantages and features of the present disclosure and methods of achieving the same will be made clear with reference to embodiments described in detail below and the accompanying drawings. However, the present disclosure may be embodied in many different forms, and should not be construed as being limited to the embodiments set forth. The embodiments are provided to make the present disclosure complete and to allow those skilled in the art to fully understand the scope of the present disclosure, in which the present disclosure is defined by the appended claims. Like reference numerals refer to like elements throughout the specification. The term "and/or" includes any combination of each described item and one or more described items.

Although the terms such "first" or "second" may be used herein to describe various elements, components and/or sections, the elements, the components and/or the sections should not be limited by the terms. The terms are only used to distinguish one element, component, or section from another element, component, or section. Therefore, a first element, a first component, or a first section, which will be described below, may be a second element, a second component, or a second section without departing from the spirit of the present disclosure.

In addition, an identification symbol (e.g., a, b, c, etc.) is used in each operation for convenience of description. The identification symbols do not represent an order of operations, and the operations may be performed in an order different from a described order unless the context explicitly indicates a specific order. That is, operations may be performed in the same order as described, may be substantially performed at the same time, or may be performed in a reverse order.

Terms used herein are intended to describe embodiments, and should not be construed as limiting the present disclosure. In the specification, singular forms are intended to include plural forms unless explicitly described otherwise in the context. The terms "comprises" and/or "comprising" used herein with components, operations, actions, and/or elements shall not be construed to preclude the presence or addition of one or more other components, operations, actions, and/or elements.

Unless defined otherwise, all terms (including technical and scientific terms) used herein may be used with the meaning which can be commonly understood by those skilled in the art. In addition, commonly-used terms, which are defined in a dictionary, should not be interpreted ideally or excessively unless explicitly defined otherwise.

In addition, in the following description of the present disclosure, the detailed description of known functions or configurations incorporated herein will be omitted when it may make the subject matter of the present disclosure rather unclear. In addition, the following terms are defined in consideration of functions in embodiments of the present disclosure, and may vary depending on the intention of a user or an operator, the custom, or the like. Therefore, the terms should be defined based on the contents throughout the specification.

FIG. 1 is a configuration diagram of a system for non-contact measurement of optoelectronic properties of a thin film according to an exemplary embodiment of the present disclosure.

Referring to FIG. 1, a system 100 for non-contact measurement of optoelectronic properties includes a sensing element 110, a thin film 120, and an optoelectronic property measuring server 130.

Figure 2:
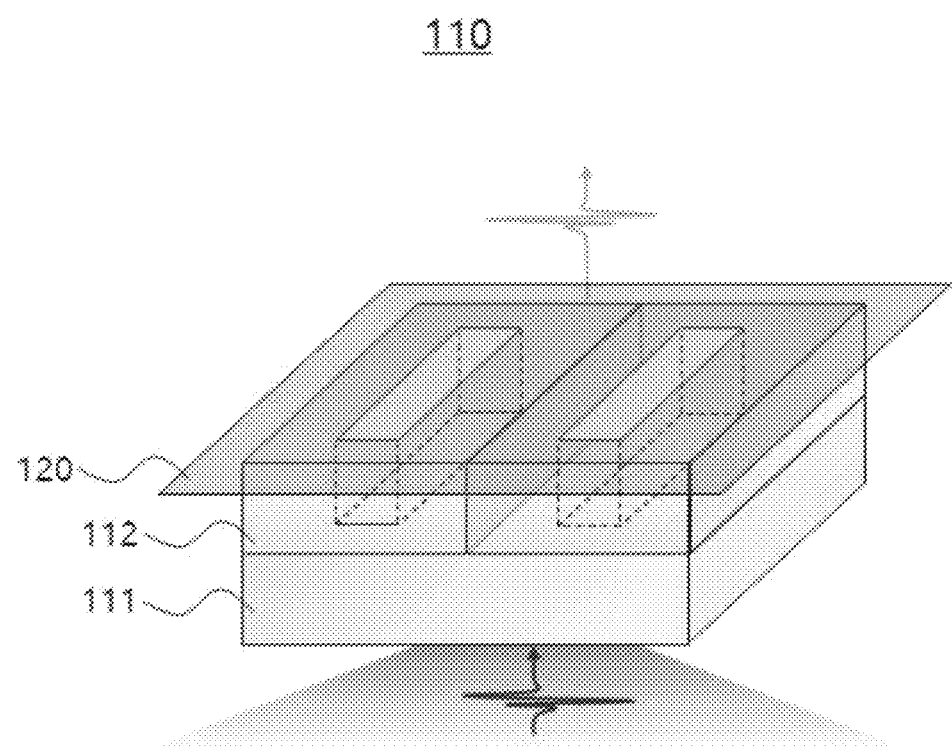
FIG. 2 is a view illustrating a structure of a sensing element according to one embodiment.
Figure 3:
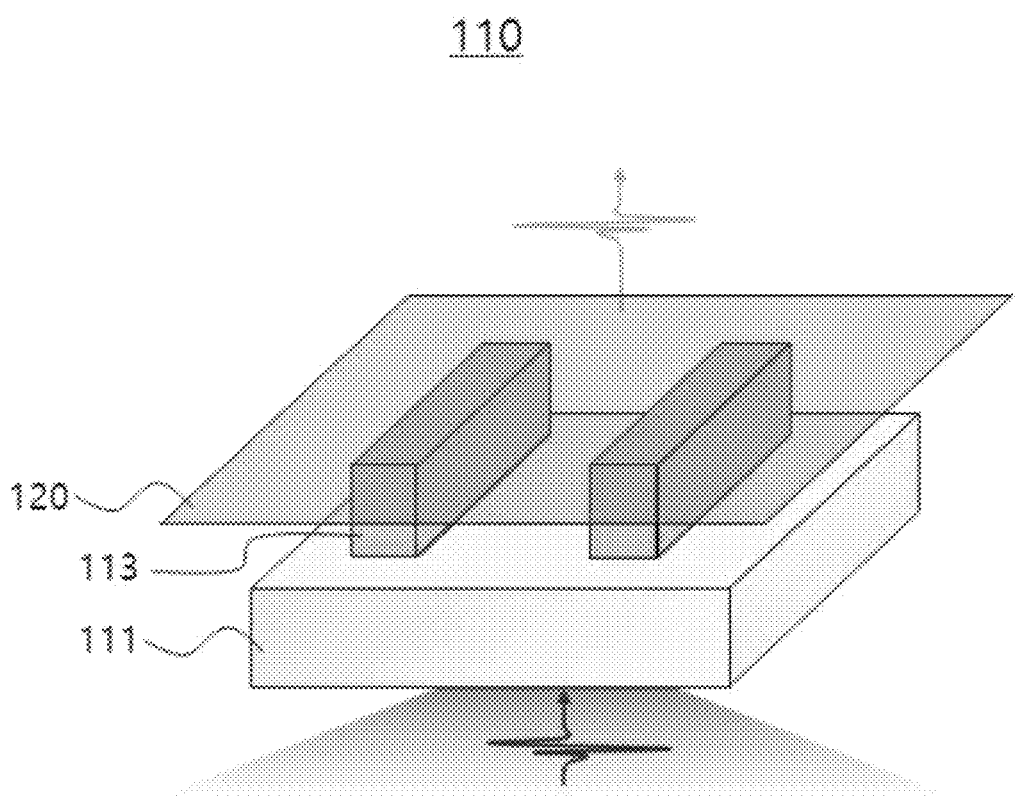
FIG. 3 is a view illustrating a structure of a sensing element according to another embodiment.

The sensing element 110 is an element configured to amplify an electromagnetic wave having a specific frequency. Referring to FIG. 2, the sensing element 110 may include a substrate 111, and a film 112 disposed on the substrate 111, wherein an engraved patterned rectangular slot may be included in the film 112 to amplify the electromagnetic wave having the specific frequency. Referring to FIG. 3, the sensing element 110 may include a substrate 111, and a film 113 disposed on the substrate 111, wherein an embossed patterned rectangular structure may be included in the film 113 to amplify the electromagnetic wave having the specific frequency.

In this case, the substrate 111 of the sensing element 110 may be formed of quartz, silicon, sapphire, or glass, and the films 112 and 113 may be formed of gold, silver, copper, or aluminum. In addition, the slot or the structure of the film 112 or 113 of the sensing element 110 may be adjusted in width, thickness, and length according to a frequency of an electromagnetic wave used to extract optoelectronic properties of the thin film 120. Since a resonance frequency may be adjusted according to the width (10 nm to 1 μm), the thickness (100 nm to 1 μm), and the length (10 μm to 1 mm) of the slot or the structure, a filter for a broadband electromagnetic wave may be designed using the sensing element 110 consisting of the slot or the structure.

The thin film 120 is a target disposed on the sensing element 110 such that the optoelectronic properties of the thin film 120 are measured. In this case, since the thin film 120 is not in contact with the substrate 111 due to configurations of the films 112 and 113 of the sensing element 110, an intrinsic property of a material of the thin film 120 may be measured with minimized external influences.

The optoelectronic property measuring server 130 is a device configured to measure the optoelectronic properties of the thin film 120 obtained when the electromagnetic wave amplified by the sensing element 110 passes through the thin film 120. Preferably, when the electromagnetic wave generated from a light source reaches a detection device (not shown in the drawings) after passing through the sensing element 110, the detection device may convert a signal of the electromagnetic wave into an electrical signal, and the optoelectronic property measuring server 130 may receive the electrical signal from the detection device to measure the optoelectronic properties of the thin film 120 from the electrical signal. In this case, the detection device may correspond to a separate device connected to the optoelectronic property measuring server 130 in a wireless or wired manner, or may be implemented as a module provided in the optoelectronic property measuring server 130.

In one embodiment, the optoelectronic property measuring server 130 may measure a band transition according to a frequency band of light passing through the sensing element 110, and may separately measure properties of an inter-band transition and intra-band transition according to the length of the slot and the structure of the sensing element 110. For example, electrons of the thin film 120 are subject to the band transition in the case that a light source in use has an energy higher than that of a mid-infrared ray because the energy of a photon is relatively high, and the electrons are not subject to the band transition in the case that a light source in use has an energy lower than that of terahertz radiation, so that the optoelectronic property measuring server 130 may measure the optoelectronic properties of the thin film using the light source having an energy lower than that of terahertz radiation without causing a change in a state of the thin film. In addition, when the lengths of the slot and the structure of the sensing element 110 are adjusted to match the resonance frequency of the light source in use, the optoelectronic property measuring server 130 may separately measure the inter-band transition and the intra-band transition.

Figure 4:
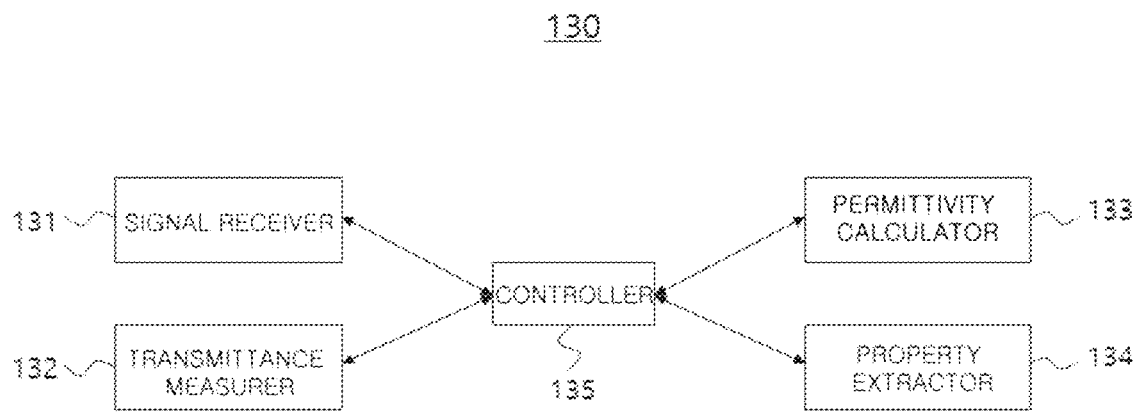
FIG. 4 is a block diagram of an optoelectronic property measuring server according to one embodiment.

FIG. 4 is a block diagram of an optoelectronic property measuring server according to one embodiment.

Figure 5:
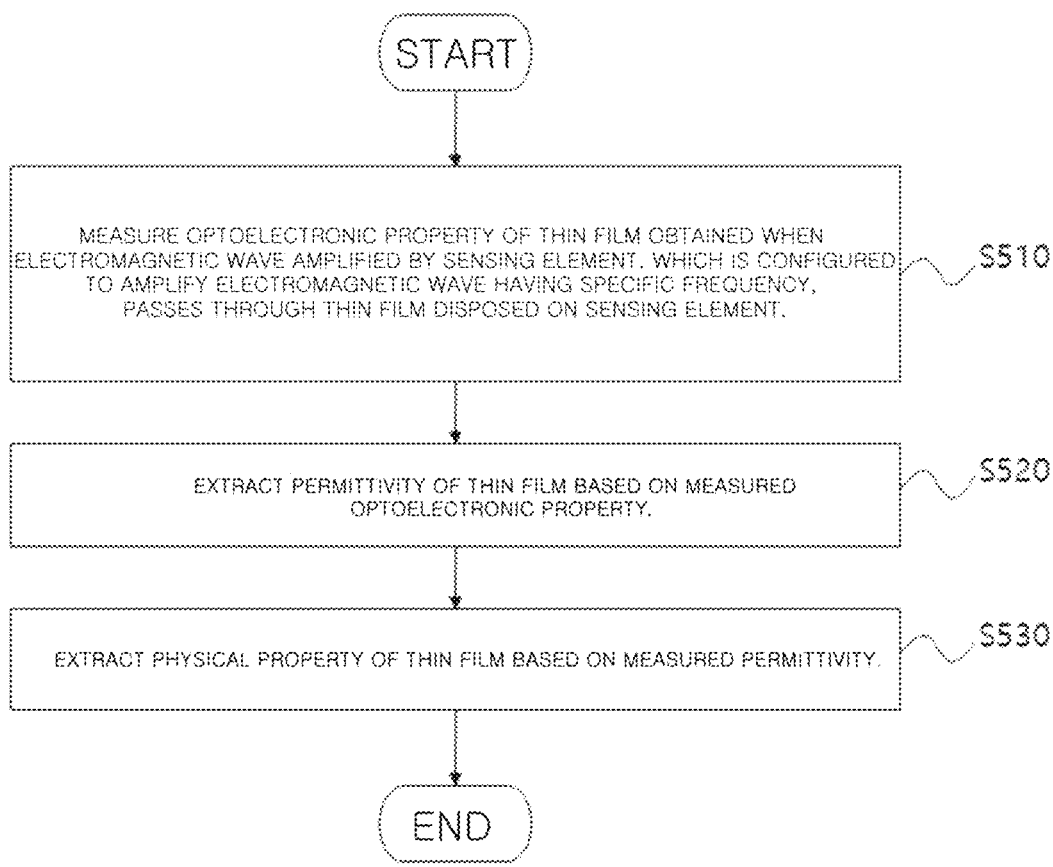
FIG. 5 is a flowchart illustrating an optoelectronic property measuring method according to one embodiment.

Referring to FIG. 4, the optoelectronic property measuring server 130 includes a signal receiver 131, a transmittance measurer 132, a permittivity calculator 133, a physical property extractor 134, and a controller 135, wherein the controller 135 controls the operation of the signal receiver 131, the transmittance measurer 132, the permittivity calculator 133, and the physical property extractor 134, and a flow of data. Hereinafter, the optoelectronic property measuring method performed in the optoelectronic property measuring server 130 will be described in more detail with reference to FIG. 5.

Figure 6:
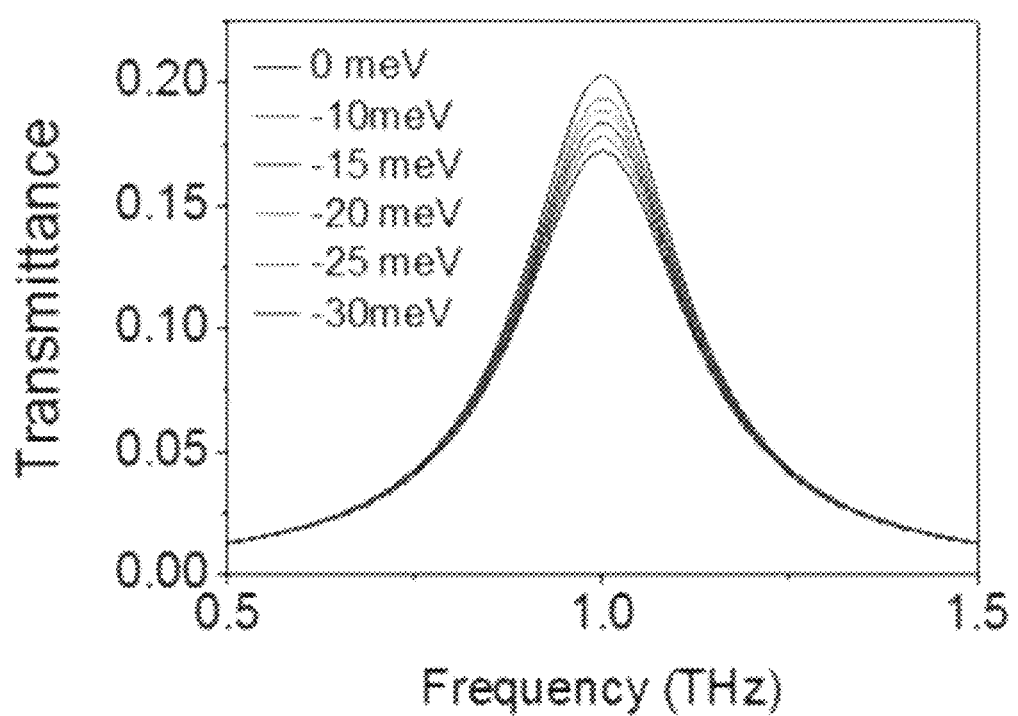
FIG. 6 is a graph illustrating a change in a transmittance according to transmission and reflection signals.

First, when an electromagnetic wave generated from a light source is amplified while passing through the sensing element 110, and the amplified electromagnetic wave passes through the thin film 120 disposed on the sensing element 110, the detection device detects the electromagnetic wave signal that has passed through the thin film 120 to convert the electromagnetic wave signal into an electrical signal, and transmits the electrical signal to the signal receiver 131. The electrical signal received by the signal receiver 131 is provided to the transmittance measurer 132, and the transmittance measurer 132 measures the optoelectronic properties of the thin film 120 based on the electrical signal (operation S510). Preferably, transmission and reflection signals obtained when the electromagnetic wave amplified by the sensing element 110 is optically transmitted through or reflected from the thin film 120 may be measured and transmitted to the signal receiver 131, and the transmittance measurer 132 may measure a transmittance of the thin film 120 based on the transmission and reflection signals. In this case, since reflectance and transmittance have the relation represented by {reflectance+transmittance=1}, the reflectance or the transmittance may be measured as the optoelectronic properties of the thin film 120. The number of electrons contributing to the transmittance, the reflectance, and conductivity varies according to a Fermi level (0 meV, −10 meV, −15 meV, . . . , −30 meV) of the thin film 120, so that the transmittance of the thin film 120 may vary. For example, as shown in FIG. 6, even when the same thin film 120 is used, transmittance graphs may be different from each other depending on the Fermi level. That is, as the transmission and reflection signals for the thin film 120 may vary due to charge dynamic properties of the thin film 120, the Fermi level of the thin film 120 is changed when the thin film 120 is doped or contaminated, and the transmittance that varies depending on the Fermi level is measured by the transmittance measurer 132.

Figure 7A:
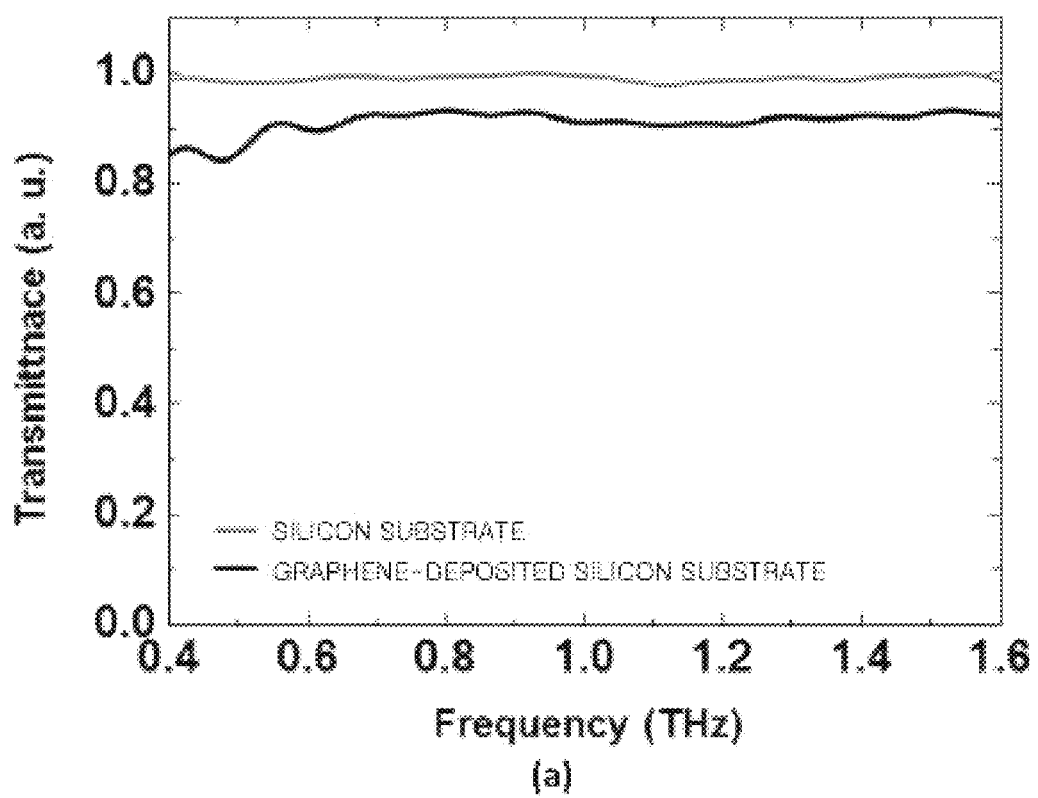
FIGS. 7A and 7B are graphs illustrating changes in an optical signal measured according to the related art and the present disclosure.
Figure 7B:
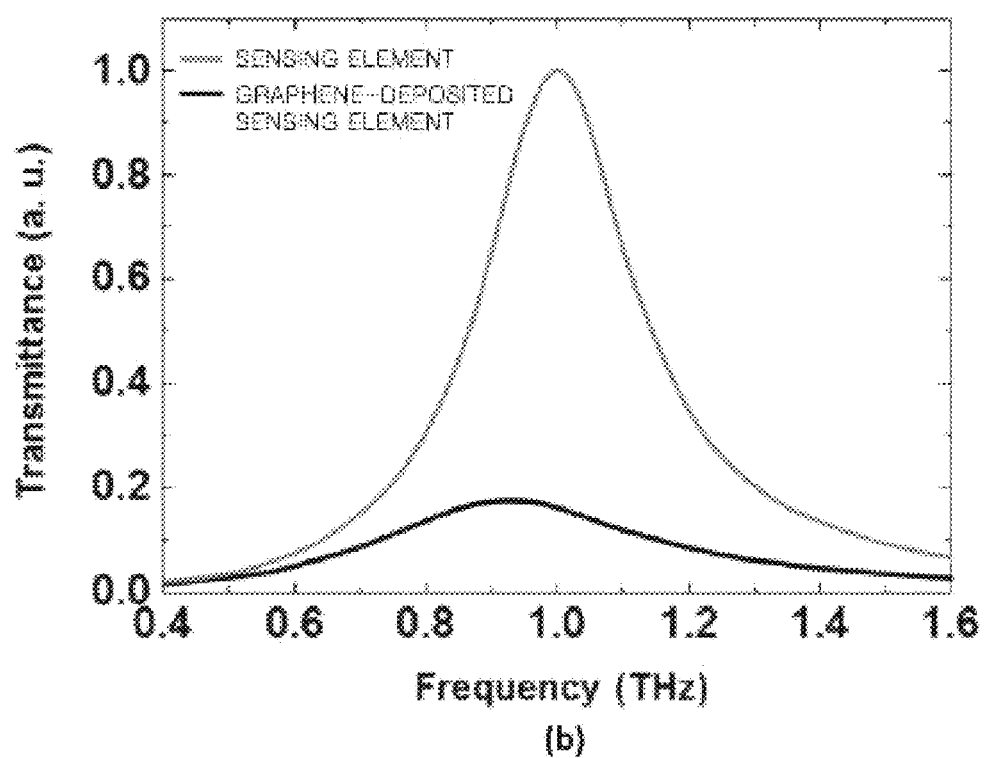

According to the present disclosure, the electromagnetic wave in a peripheral band of the resonance frequency, which is adjusted according to the configuration of the slot or the structure formed in the sensing element 110, is incident on the sensing element 110, the incident electromagnetic wave is amplified in the slot or the structure, and a quantum-mechanical absorption sectional area of the thin film 120 is increased by the amplified electromagnetic wave, so that optical signal modulation may be greatly amplified so as to increase sensitivity to a high level. For example, referring to FIG. 7A, in a conventional case of using a silicon substrate or a graphene-deposited silicon substrate, the sensitivity is low and the transmittance is rarely changed. However, referring to FIG. 7B, in the case of using the sensing element 110 according to the present disclosure, changes of the transmission and reflection signals, which are optically transmitted and reflected, are greatly amplified by an increase in the absorption sectional area due to the amplification of electromagnetic waves, resulting in a great change in the transmittance. That is, when the sensing element 110 according to the present disclosure is used, a change in optical properties of the thin film 120 may be easily detected.

The permittivity calculator 133 calculates a permittivity of the thin film 120 based on an optoelectronic property measured by the transmittance measurer 132, that is, the transmittance (operation S520). Preferably, the permittivity calculator 133 may calculate the permittivity of the thin film 120 based on the measured transmission and reflection signals. Hereinafter, an operation of calculating the permittivity through the transmittance measurer 132 and the permittivity calculator 133 will be described in more detail.

Before the transmittance of the thin film 120 is measured by the transmittance measurer 132, the transmittance measurer 132 measures the transmittance of the sensing element 110 before the thin film 120 is disposed. That is, the transmittance of the slot or the structure of the sensing element 110 is measured, for example, as indicated by a dotted line in FIG. 8A. The transmittance measurer 132 simulates the configuration of the sensing element 110 to obtain a simulation result of the transmittance of the slot or the structure of the sensing element 110. In this case, the simulation result may be calculated using a finite element method (FEM), a finite difference time domain (FDTD) method, single mode approximation, or the like, and obtained, for example, as indicated by a red solid line in FIG. 8A. The transmittance measurer 132 adjusts the conductivity of a metal thin film used in the slot or the structure of the sensing element 110 to match the simulated transmittance with the measured transmittance.

Figure 8A:
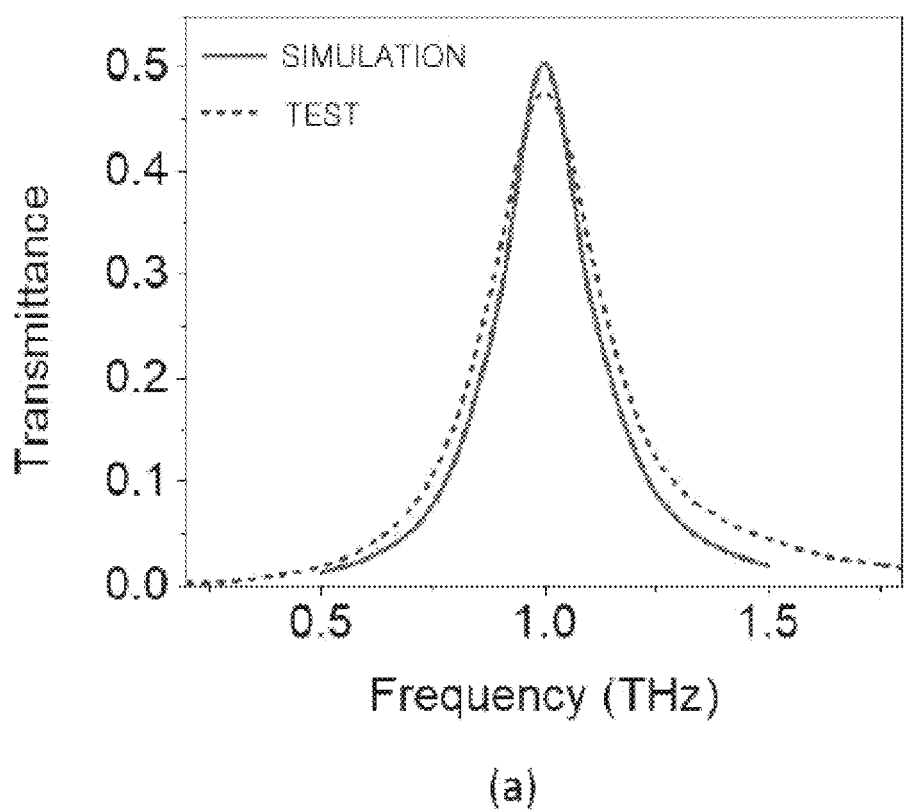
FIGS. 8A and 8B are graphs for describing an operation of calculating a permittivity.
Figure 8B:
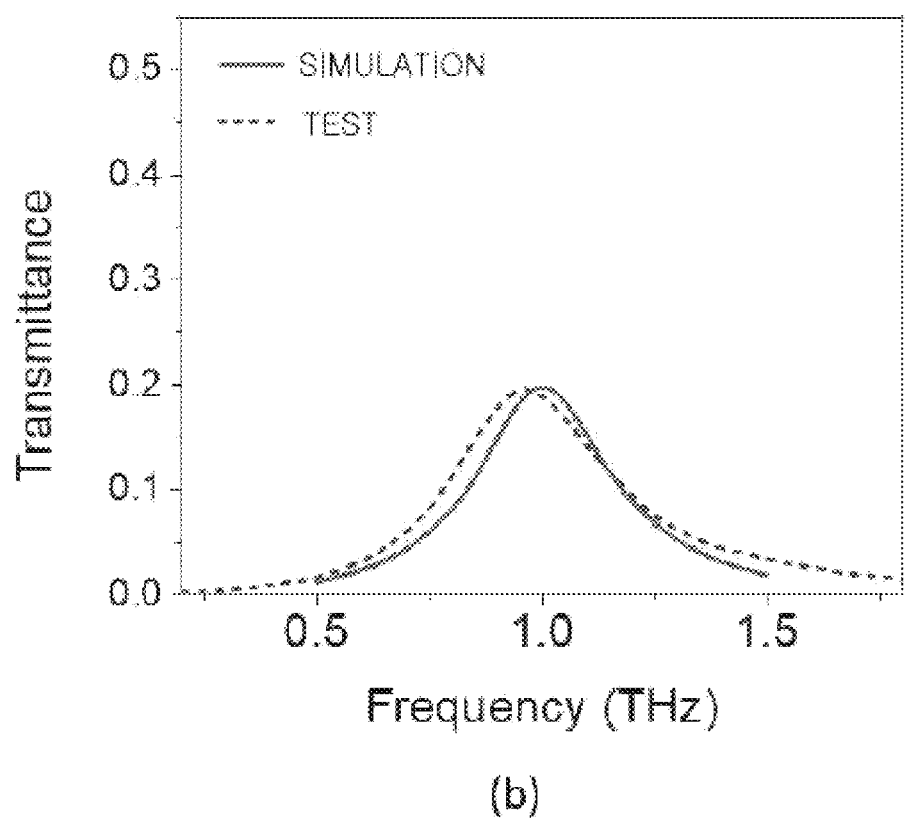

Next, the thin film 120 is disposed on the sensing element 110, and the transmittance measurer 132 measures the transmittance of the thin film 120 disposed on the sensing element 110 as described above. For example, the transmittance of the thin film 120 may be measured as indicated by a dotted line in FIG. 8B. The transmittance measurer 132 measures the transmittance by adding the configuration of the thin film 120 to the simulated configuration of the sensing element 110. That is, the conductivity of the metal thin film in FIG. 8A is adjusted, and the thin film 120 is disposed in the simulated configuration to which the measured transmittance is applied such that conditions are set identical to a case in which the transmittance is measured by a test as shown in FIG. 8B, thereby obtaining the simulation result for the transmittance of the thin film 120. For example, the transmittance as indicated by a red solid line in FIG. 8B may be obtained as the simulation result.

The permittivity calculator 133 calculates the permittivity of the thin film 120 based on the transmittance of the thin film 120 measured by the test and obtained by the transmittance measurer 132, and the transmittance of the thin film 120 obtained as the simulation result. Preferably, the permittivity calculator 133 may calculate the permittivity of the thin film 120 for matching the simulated transmittance to the tested transmittance, for example, the permittivity for matching the simulated transmittance indicated by the red solid line to the measured transmittance indicated by the dotted line in FIG. 8A.

The physical property extractor 134 extracts physical properties of the thin film 120 based on the permittivity calculated by the permittivity calculator 133 (operation S530). In this case, the physical properties of the thin film 120 may correspond to the Fermi level, charge density, or charge mobility, and the physical properties may vary depending on a doping level and an ion implantation amount of the thin film 120. Preferably, the physical property extractor 134 applies the permittivity calculated by the permittivity calculator 133 to the Kubo formula to model the permittivity for the inter-band transition and the intra-band transition of the thin film 120 represented by Equation 1 and Equation 2 as follows.

$$\varepsilon_{intra}(\omega) = \varepsilon_x + i\frac{1}{\omega d \varepsilon_0}\left\{\frac{e^2}{\pi\hbar^2}\left(\frac{2kT}{\frac{1}{\tau} - i\omega}\right)\ln\left[2\cosh\left(\frac{eE_F}{2kT}\right)\right]\right\}$$ [Equation 1]

$$\varepsilon_{inter}(\omega) = \varepsilon_x + i\frac{1}{\omega d \varepsilon_0}\left\{\frac{e^2}{2\pi\hbar^2}\int_o^\infty \frac{\sinh x}{\cosh\left(\frac{eE_F}{kT}\right) + \cosh x}\frac{\hbar\left(\omega + \frac{i}{\tau}\right)}{x^2 + \left(\frac{\hbar\left(\omega + \frac{i}{\tau}\right)}{2kT}\right)^2}\right\}$$ [Equation 2]

In the above equations, ω denotes a frequency, d denotes the thickness of the thin film 120, $\hbar$ denotes the reduced Planck constant, $\varepsilon_0$ denotes a permittivity in a vacuum, k denotes the Boltzmann constant, T denotes a temperature (K), e denotes an elementary quantum of electricity, τ denotes a mean free time, and $E_F$ denotes the Fermi level.

In addition, the physical property extractor 134 may calculate the charge mobility and the electron density of the thin film 120 represented by Equation 3 and Equation 4 as follows by using the permittivity calculated by the permittivity calculator 133 and parameters used for calculating the permittivity, that is, parameters used to match the permittivity measured as a result of the test with the simulated permittivity.

$$\mu = \frac{v_F^2 \tau e}{E_F}$$ [Equation 3]

$$n = \frac{\left(\frac{E_F}{\hbar v_F}\right)^2}{\pi}$$ [Equation 4]

In the above equations, μ denotes the charge mobility, $v_F$ denotes a Fermi velocity, τ denotes the mean free time, e denotes the elementary quantum of electricity, $E_F$ denotes the Fermi level, n denotes the electron density, and h denotes the reduced Planck constant.

Figure 9:
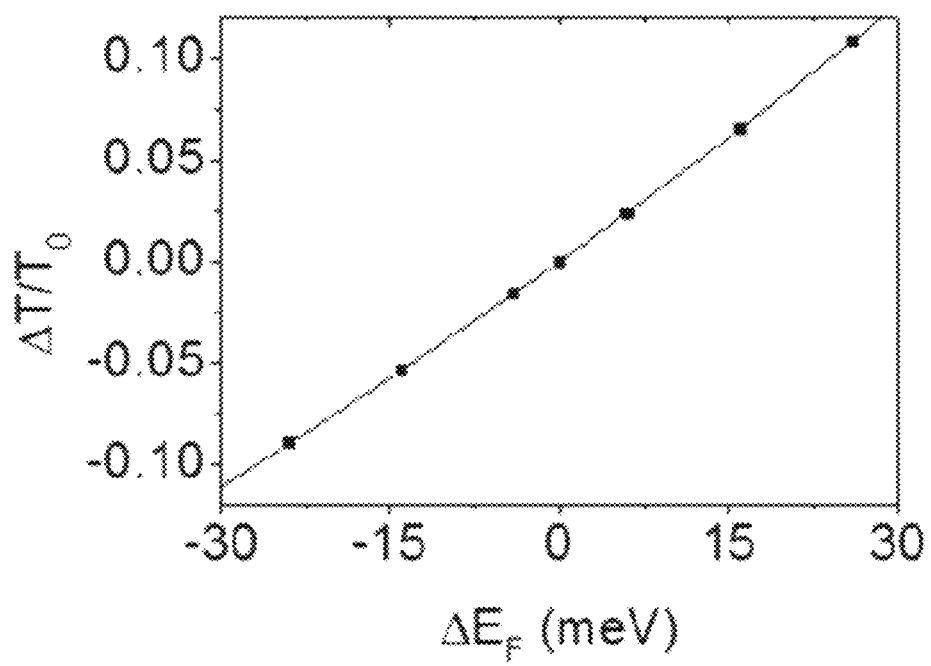
FIG. 9 is a graph illustrating the relation between a rate of change of the transmittance and an amount of change in a Fermi level.
Figure 10:
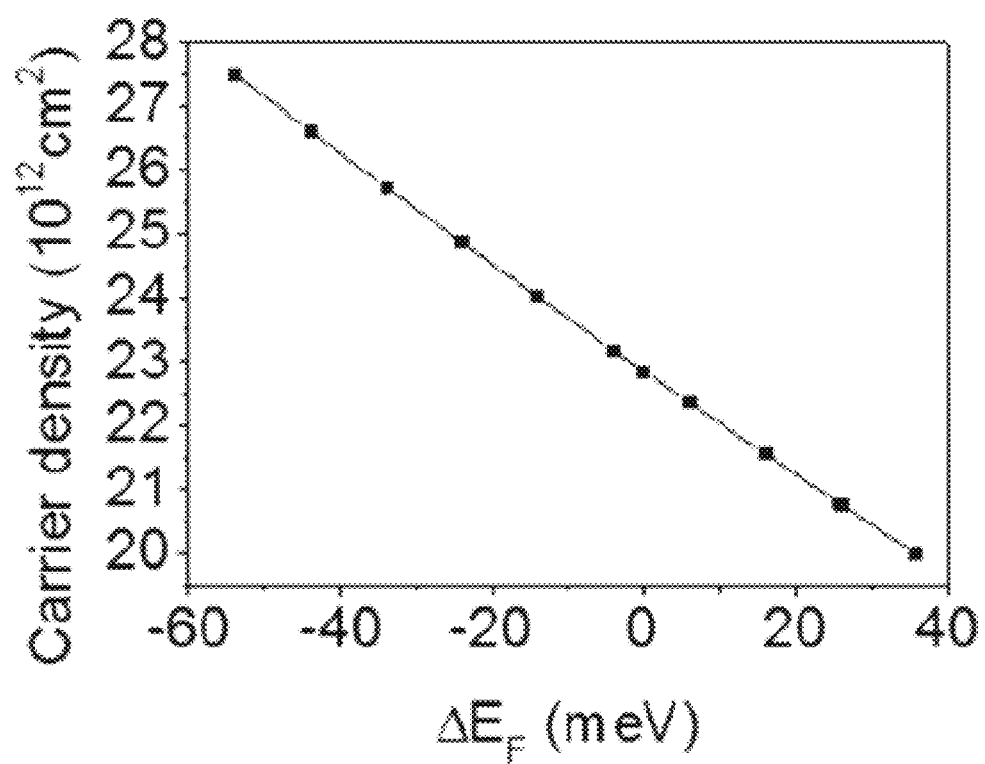
FIG. 10 is a graph illustrating the relation between a charge density and the amount of change in the Fermi level.

Therefore, the physical property extractor 134 may extract the Fermi level, the charge density, the charge mobility, and the like by applying the permittivity to a theoretical model for the permittivity of the material of the thin film 120. For example, the physical property extractor 134 may apply the permittivity to the Kubo formula to obtain the relation between a rate of change of the transmittance and an amount of change in the Fermi level as shown in FIG. 9, and the relation between the charge density and the amount of change in the Fermi level as shown in FIG. 10. In addition, the physical property extractor 134 may calculate the doping level and the ion implantation amount of the thin film 120 by applying the extracted Fermi level, the extracted charge density, the extracted charge mobility, and the like to the theoretical model of the material of the thin film 120.

Figure 11A:
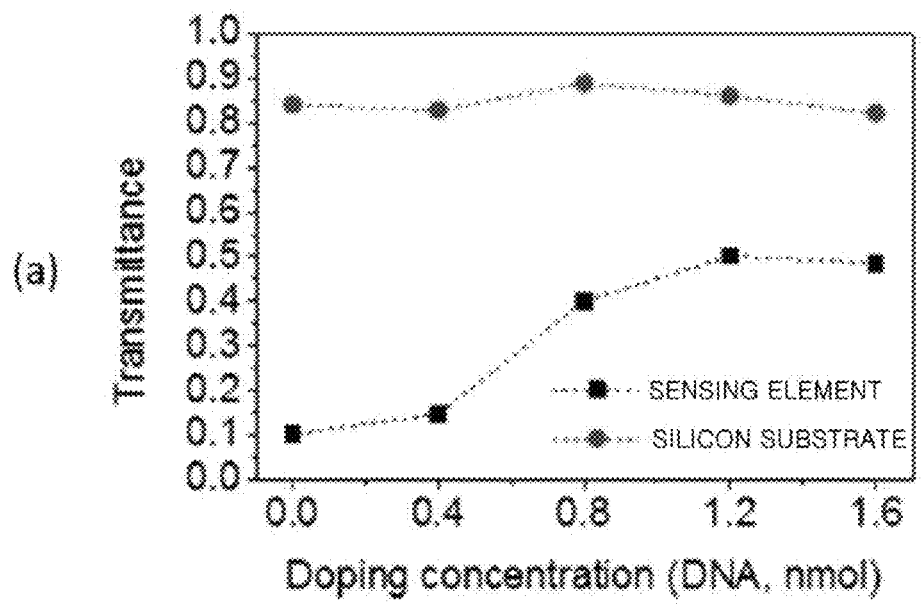
FIGS. 11A and 11B are graphs illustrating changes in the transmittance and physical properties measured according to the related art and the present disclosure.
Figure 11B:
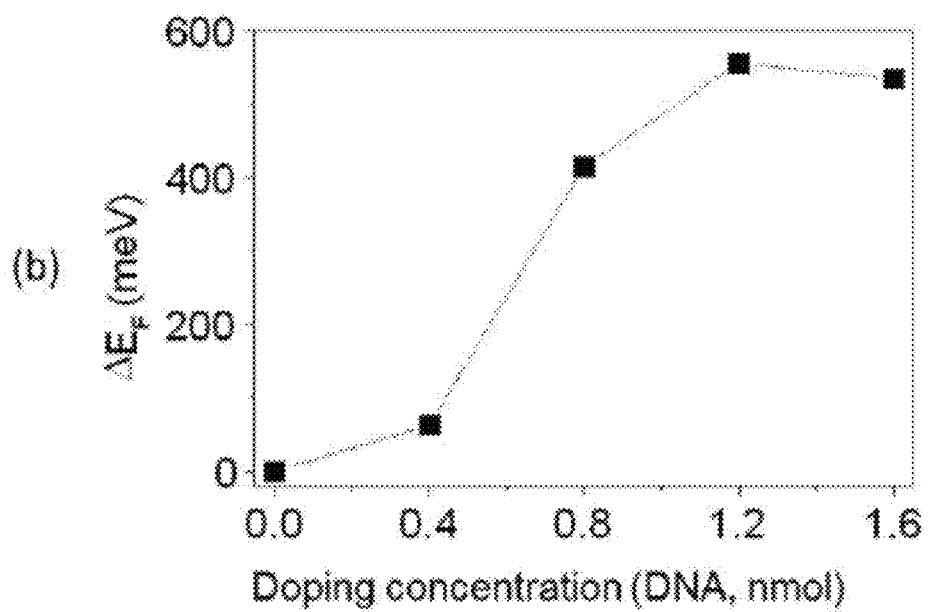

FIGS. 11A and 11B are graphs illustrating changes in the transmittance and physical properties measured according to the related art and the present disclosure.

Referring to FIGS. 11A and 11B, FIG. 11A is a graph illustrating the transmittance change according to concentration when graphene is chemically doped using DNA, where it is difficult to observe the transmittance change in the case of using a conventional silicon substrate, whereas the transmittance change is great in the case of using the sensing element 110 according to the present disclosure.

As described above, the intrinsic property of the material of the thin film 120 as shown in FIG. 11B may be extracted by comparing and analyzing the amplified optical properties obtained by the sensing element 110 with a result obtained through the modeling and applying a theoretical background of the material of the thin film. That is, after the permittivity of the thin film 120 is calculated based on the transmittance of the thin film 120 measured by the test and the transmittance of the thin film 120 measured by the simulation, the physical properties of the thin film 120 are extracted by applying the permittivity to the theoretical model of the material of the thin film 120.

For example, graphene, which is a representative two-dimensional material, is a carbon material with a single atomic layer having a thickness of 0.34 nm and arranged in a hexagon, exhibits properties of the inter-band transition in a far-infrared band (terahertz frequency band), and exhibits properties of the inter-band transition in a mid-infrared band. According to the related art, since the transmittance change is 10% or less when the inter-band transition is measured using a terahertz electromagnetic wave in order to prevent the Fermi level from being changed due to a photon, the transmittance change due to the doping of the thin film is observed to be remarkably small, which may result in an error. However, when the sensing element 110 having the slot or the structure optimized to the terahertz band is applied according to the present disclosure, since the transmittance change is amplified several ten-fold, a signal intensity is sensitively changed due to the doping of the thin film, so that changes of physical properties may be precisely observed.

Meanwhile, the method for non-contact measurement of the optoelectronic properties of the thin film according to one embodiment of the present disclosure may be implemented as computer-readable code on a computer-readable recording medium. The computer-readable recording medium includes all types of recording devices in which data that can be read by a computer system is stored.

For example, the computer-readable recording medium may be a read-only memory (ROM), a random-access memory (RAM), a CD-ROM, a magnetic tape, a hard disc, a floppy disk, a removable storage device, a nonvolatile memory (flash memory), an optical data storage device, and the like.

In addition, the computer-readable recording medium may be stored and executed as code which is readable in a distributed manner by being distributed in a computer system connected to a computer network.

As is apparent from the above description, since the optoelectronic properties of the thin film are measured in a non-contact manner, inaccuracy or loss of signals due to contact with the electrode, which has been a disadvantage of conventional electrical measurement, can be overcome. In addition, changes due to the inter-band transition and the intra-band transition of the thin film can be distinguished from each other according to a wavelength band of the light source, so that the physical properties can be accurately extracted.

In addition, the slot or the structure of the sensing element is a structure having a level of nanometers to micrometers, in which the resonance frequency can be tuned in a wide frequency range through various patterns using the slot or the structure, and the electromagnetic wave is amplified in the configuration of the sensing element when the electromagnetic wave in the peripheral band of the resonance frequency is incident, which leads to an increase in a quantum-mechanical absorption sectional area of a sample molecule. Therefore, the sensitivity can be increased to a higher level than that of a conventional spectroscopic analysis method, so that the present disclosure can be applied to detect a minute amount of a sample.

Therefore, according to the present disclosure, a two-dimensional material having optoelectronic properties to be measured does not come into contact with the substrate due to the slot or the structure, so that the properties of the two-dimensional material can be measured by a non-contact and optical method without an influence of the substrate. In addition, the electromagnetic wave amplified through the configuration of the sensing element is used to sensitively measure the properties changed by manipulation such as the doping, so that intrinsic properties of a material can be measured with minimized external influences.

Although the system and method for non-contact measurement of measuring optoelectronic properties of the thin film according to exemplary embodiments of the present disclosure have been described, the present disclosure is not limited thereto, and it will be understood that changes may be variously made in the claims, the detailed description of exemplary embodiments, and the accompanying drawings without departing from the spirit and scope of the present disclosure.

What is claimed is:

1. A system for non-contact measurement of an optoelectronic property, the system comprising:
   a sensing device configured to amplify an electromagnetic wave having a specific frequency, the sensing device including
      a substrate, and
      a film disposed on the substrate, wherein the film comprises a patterned rectangular slot engraved in the film or a patterned rectangular structure embossed on the film to amplify the electromagnetic wave having the specific frequency, wherein material characteristic of the substrate is different from material characteristic of the film;
   a thin film disposed over the sensing device to measure an optoelectronic property of the thin film; and
   an optoelectronic property measuring server configured to extract a physical property of the thin film based on the optoelectronic property of the thin film obtained in response to detection of amplification of the electromagnetic wave amplified by the sensing device passes through the thin film.

2. The system of claim 1, wherein each of the patterned rectangular slot engraved in the film or the patterned rectangular structure embossed on the film has a width, a thickness, and a length, which are adjusted according to a frequency of an electromagnetic wave used for extracting the optoelectronic property of the thin film.

3. The system of claim 1, wherein the optoelectronic property measuring server measures a transmittance based on transmission and reflection signals obtained when the amplified electromagnetic wave is optically transmitted through the thin film or reflected from the thin film.

4. The system of claim 3, wherein the optoelectronic property measuring server calculates a permittivity of the thin film based on the measured transmittance.

5. The system of claim 4, wherein the optoelectronic property measuring server extracts a Fermi level, a charge density, or a charge mobility, which corresponds to the physical property of the thin film, based on the permittivity.

6. The system of claim 5, wherein the optoelectronic property measuring server determines a doping level and an ion implantation amount of the thin film based on the physical property of the thin film.

7. A method for non-contact measurement of an optoelectronic property performed in a system for non-contact measurement of an optoelectronic property, the method comprising:
    measuring an optoelectronic property of a thin film obtained when an electromagnetic wave amplified by a sensing device by amplifying an electromagnetic wave having a specific frequency, passes through the thin film disposed over the sensing device; and
    extracting a physical property of the thin film based on the measured optoelectronic property, wherein the sensing device includes
      a substrate, and
      a film disposed on the substrate, wherein the film comprises a patterned rectangular slot engraved in the film or a patterned rectangular structure embossed on the film to amplify the electromagnetic wave having the specific frequency, wherein material characteristic of the substrate is different from the material characteristic of the film.

8. The system of claim 1, wherein the material characteristic of the substrate comprises at least one of quartz, silicon, sapphire, and glass, the material characteristic of the film comprises at least one of gold, silver, copper, or aluminum.

9. The system of claim 2, wherein each of the patterned rectangular slot engraved in the film or the patterned rectangular structure embossed on the film includes a 10 nm to 1 μm width, 100 nm to 1 μm thickness, and 10 μm to 1 mm length.

10. The method of claim 7, further comprising:
    measuring a transmittance based on transmission and reflection signals obtained when the amplified electromagnetic wave is optically transmitted through the thin film or reflected from the thin film.

11. The method of claim 10, further comprising:
    calculating a permittivity of the thin film based on the measured transmittance.

12. The method of claim 11, further comprising:
    extracting a Fermi level, a charge density, or a charge mobility, which corresponds to the physical property of the thin film, based on the permittivity.

13. The method of claim 12, further comprising:
    determining a doping level and an ion implantation amount of the thin film based on the physical property of the thin film.

14. The method of claim 7, wherein each of the patterned rectangular slot engraved in the film or the patterned rectangular structure embossed on the film has a width, a thickness, and a length, which are adjusted according to a frequency of an electromagnetic wave used for extracting the optoelectronic property of the thin film.

15. A computer-readable recording medium having a program causing a computer to execute the method of claim 7.

* * * * *